(12) United States Patent
Musha

(10) Patent No.: US 6,349,231 B1
(45) Date of Patent: Feb. 19, 2002

(54) METHOD AND APPARATUS FOR WILL DETERMINATION AND BIO-SIGNAL CONTROL

(75) Inventor: Toshimitsu Musha, Machida (JP)

(73) Assignee: Brain Functions Laboratory, Inc., Kawasaki (JP)

( * ) Notice: Subject to any disclaimer, the term of this patent is extended or adjusted under 35 U.S.C. 154(b) by 0 days.

(21) Appl. No.: 08/904,043

(22) Filed: Jul. 31, 1997

Related U.S. Application Data

(63) Continuation-in-part of application No. 08/799,558, filed on Feb. 10, 1997, now abandoned, which is a continuation of application No. 08/274,196, filed on Jul. 12, 1994, now Pat. No. 5,601,090.

(30) Foreign Application Priority Data

Jan. 12, 1994 (JP) .................................................. 6-1567
Mar. 4, 1997 (JP) .............................................. 9-049368

(51) Int. Cl.[7] .............................................. A61B 5/00
(52) U.S. Cl. ........................ 600/544; 600/546; 600/300
(58) Field of Search ................................ 600/544, 5, 6, 600/7, 600, 300

(56) References Cited

U.S. PATENT DOCUMENTS

| | | | | |
|---|---|---|---|---|
| 4,926,969 A | * | 5/1990 | Wright et al. | 600/544 |
| 5,474,082 A | * | 12/1995 | Junker | 600/545 |
| 5,638,826 A | * | 6/1997 | Wolpaw | 600/545 |
| 5,687,291 A | * | 11/1997 | Smyth | 600/544 |
| 5,762,611 A | * | 6/1998 | Lewis et al. | 600/545 |
| 6,070,098 A | * | 5/2000 | Moore-Ede et al. | 600/544 |

* cited by examiner

Primary Examiner—Robert L. Nasser
(74) Attorney, Agent, or Firm—Rader, Fishman & Grauer, PLLC

(57) ABSTRACT

An apparatus and a method for automatically determining the present will of a human subject. The characteristic values of the subject are detected and output signals corresponding to the detected characteristic values are produced, amplified and digitized. A set of state variables for each selected frequency sub-band of a selected frequency band for each of the output signals is determined. Sets of reference weights and sets of reference biases for a neural network from sets of state reference variables corresponding to known wills are formed. Each of the sets of state variables, the sets of reference weights and the sets of reference biases are applied to the neural network to determine present will of the subject. The present will of the subject can be displayed or used to control an external device, such as a robot.

33 Claims, 3 Drawing Sheets

METHOD AND APPARATUS FOR WILL DETERMINATION AND BIO-SIGNAL CONTROL

CROSS REFERENCE TO RELATED APPLICATION

This is a continuation-in-part of U.S. patent application Ser. No. 08/799,558, filed Feb. 10, 1997, which is a continuation of U.S. patent application Ser. No. 08/274,196, filed Jul. 12, 1994, now U.S. Pat. No. 5,601,090.

BACKGROUND OF THE INVENTION

This invention relates to a method and an apparatus for will determination and bio-signal control, and more particularly to quantifying the will of the human subject to which the apparatus is connected and allowing the subject to control elements of his environment.

Psychologists use electroencephalographic ("EEG") waveforms to interpret the subject's mental state. This introduces subjective criteria into the analysis because a human expert is required to interpret the EEG waveforms. In addition, to being unable to analyze the subject's mental state with enough accuracy to determine the subject's will, this method is labor-intensive and time-consuming.

"Will" can be broadly defined to include not only desires and wishes but also emotions. One example of a will is the hunger will and the magnitude of that will. Other wills with magnitudes are the will to scratch one's arm, to listen to a particular song, etc. Examples of emotions include anger, sadness, joy and disgust. Wills can be further decomposed into sub-wills and magnitudes, for example, such as what kind of and how much food one wishes to eat.

There is a continuing need for means whereby a human subject's mental state can be decomposed into a, possibly infinite, discrete set of wills and corresponding magnitudes which can be expressed in matrix form. In addition to a host of applications in the human-machine interface field which would benefit from improved will determination, patients suffering with symptoms of such diseases as amyotrophic lateral sclerosis ("ALS"), who have near-normal mental function but are unable to express their will, would benefit greatly.

Examples of bio-signal control based on monitoring EEG waveforms are described in, for example, Hugh S. Lusted and R. Benjamin Knapp, "Controlling Computers with Neural Signals," *Scientific American*, pages 82–87 (October 1996) and Jonathan R. Wolpaw et al., "An EEG-Based Brain-Computer Interface For Cursor Control," *Electroencephalography and Clinical Neurophysiology*, pages 252–259 (March 1991). However, these methods of bio-signal control require training the subject to control the amplitude of a mu wave, a process that may require several days.

In view of the foregoing, it would be desirable to be able to provide a method and an apparatus for will determination and bio-signal control, and more particularly to quantifying the will of the human subject to which the apparatus is connected and allowing the subject to control elements of his environment.

SUMMARY OF THE INVENTION

It is an object of this invention to provide a method and an apparatus for will determination and bio-signal control, and more particularly to quantifying the will of the human subject to which the apparatus is connected and allowing the subject to control elements of his environment.

These and other objects of the invention are accomplished in accordance with the principles of the invention by providing a method and an apparatus for will determination and bio-signal control, and more particularly to quantifying the will of the human subject to which the apparatus is connected and allowing the subject to control elements of his environment.

Characteristic values of the subject (i.e., a set of EEG signals which may be supplemented by signals based on a combination of scalp potential, muscle potential, heart-rate, eye-movement and frequency of eye blinks, for example) are detected and corresponding output signals are produced. The output signals are then amplified and digitized. Fourier transformations or cross-correlations are performed on the digitized output signals. A set of state variables is determined for each selected frequency sub-band of a selected frequency band for each of the output signals. Each of the sets of state variables is applied to a trained neural network to determine will of the subject. The will of the subject is then displayed. In order to train the neural network, sets of reference weights and sets of reference biases are formed for a neural network using sets of state reference variables corresponding to known wills.

BRIEF DESCRIPTION OF THE DRAWINGS

The above and other objects and advantages of the invention will be apparent upon consideration of the following detailed description, taken in conjunction with the accompanying drawings, in which the reference numbers refer to like parts throughout and in which.

DETAILED DESCRIPTION OF THE INVENTION

The present invention is a method and an apparatus for will determination and bio-signal control, and more particularly to quantifying the will of the human subject to which the apparatus is connected and allowing the subject to control elements of his environment.

Characteristic values of the subject which are indicative of will are detected using sensors. Most typically, brain waves (bio-signals which can be measured by measuring scalp potential using electrodes) are used as characteristic values. In addition, bio-signals such as muscle potential, heart-rate, eye-movement and frequency of eye blinks, or combinations thereof, can be used as characteristic values.

The invention can function even if none of the above-described bio-signals are available, as long as the patient can hear. Audibility can be confirmed by observing the auditory evoked response of the EEG. If the patient has hearing in one ear only, different audio inputs, A and B, can be provided to this ear alternatively and the patient attempts to listen to either A or B, which could correspond to "yes" or "no," respectively.

Figure 1:
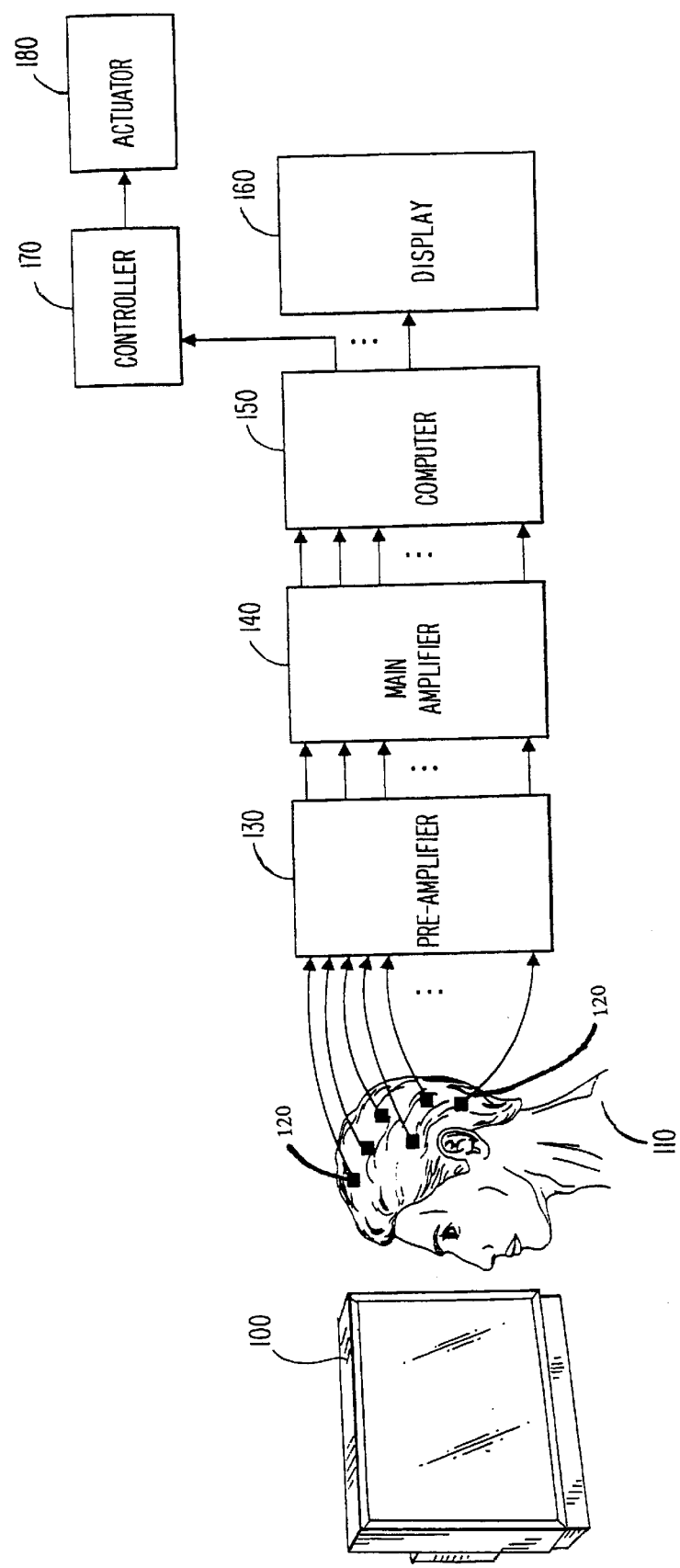
FIG. 1 is a block diagram of a hardware implementation of a preferred embodiment of the apparatus for automatically determining the will of a subject.

The sensors produce output signals corresponding to the detected characteristic values. The output signals are then amplified and digitized before being input into computer 150, as shown in FIG. 1. In order to determine the power spectral density of the output signals, Fourier transformations or cross-correlations are performed by computer 150 on the digitized output signals. Since some frequency bands are more important sources of will information, only the most important frequency bands are selected. Commonly used frequency bands correspond to alpha waves (associated with not focusing one's attention), beta waves (associated with heightened mental activity), theta waves (associated with emotional stress), delta waves (associated with deep sleep) and mu waves (associated with physical movements). Each selected frequency band is further divided into several sub-bands. A set of state variables is determined for each sub-band of each selected frequency band for each output signal power distribution. Each of the sets of state variables is applied to a trained neural network to determine will of the subject. The present will of the subject can then be displayed or, after coding, sent to controller 170, which controls actuator 180.

The neural network is trained by forming sets of reference weights and sets of reference biases from sets of state reference variables determined from output signals detected during known wills. For example, consider the process of training the neural network to recognize two wills, the two wills corresponding to "yes" and "no." In one embodiment, the subject is made to listen to two different musical pieces, one from each ear. The subject is instructed to concentrate on listening to the music in one ear for several minutes. In order to produce a set of state variables, output signals corresponding to measured characteristic values are produced, amplified and digitized. A power spectral density of the output signal from each sensor is determined by performing the Fourier transformation or a cross-correlation on the digitized output signals. A set of state reference variables for "yes" is obtained from the values of power spectral density or cross-correlation coefficients from each sub-band of the selected frequency bands. Then, after a break, the subject is instructed to concentrate on listening to the music in the other ear. The process is repeated in order to generate a set of state reference variables for "no."

The purpose of the training phase is to generate a set of reference weights and a set of reference biases that can be used to determine unknown wills such as "yes," "no" or neither. A method such as the back-propagation method with supervised learning is often employed. Initially the reference weights and the reference biases are set to random numbers. Then the set of state reference variables for "yes" is applied to the neural network and the output of the neural network is compared to the desired output (i.e., "yes") and the values of the reference weights and the reference biases are adjusted accordingly. The process is repeated for "no." In practice, the process may be repeated for many sets of reference variables corresponding to the wills of "yes" and "no" in order to further refine the reference weights and reference biases and improve the neural network's ability to recognize "yes" and "no." Ultimately, when the determination error rate has reached an acceptable level, a single set of reference weights and a single set of reference biases that can be used to determine unknown wills such as "yes," "no" or neither is generated.

The invention is not limited to distinguishing between two wills (the above described wills of "yes" and "no"). The neural network can be trained to recognize other wills (such as the will to move a computer cursor up, down, left or right, the will to input the letter "a, "b," or "c," etc.).

FIG. 1 is a block diagram of a hardware implementation of a preferred embodiment of the apparatus for automatically determining the will of subject 110. Stimulus 100, which is applied to subject 110, may be an externally applied signal such as noise, music or a television picture, or stimulus 100 can be mental images generated internally by subject 110 himself/herself. Affixed to subject 120 is a plurality of sensors 120.

Figure 2:
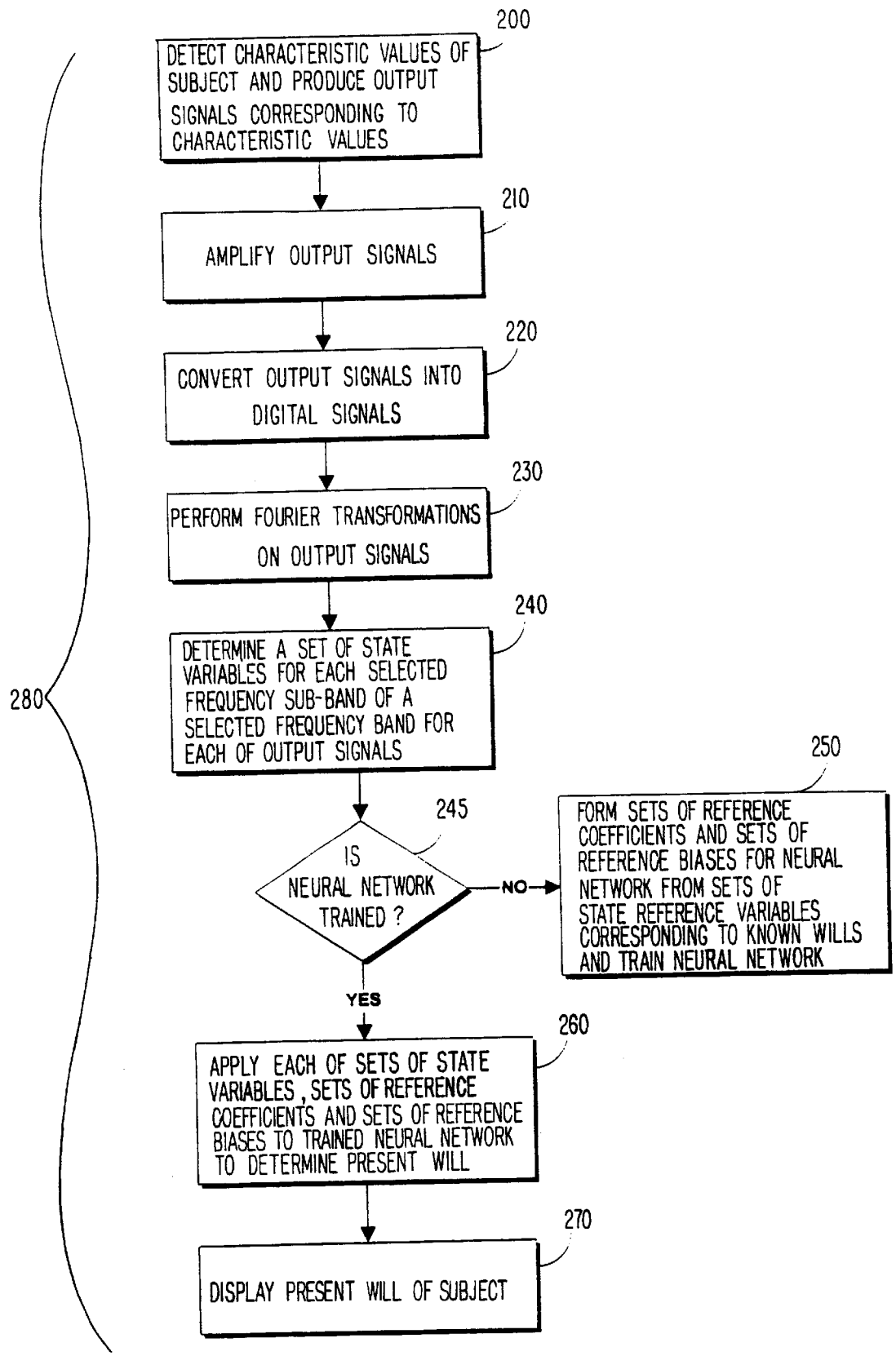
FIG. 2 is a flowchart showing the steps involved in automatically determining the will of a subject.

FIG. 2 shows the steps involved in process 280 of automatically determining the will of subject 110. In step 200, sensors 120 detect characteristic values of subject 110. Characteristic values refer to those traits, such as scalp potential, muscle potential, heart-rate, eye-movement and frequency of eye blinks of subject 110, which are indicative of subject's 110 present will. Indeed, any combination of such characteristic values can be used.

In step 210 of process 280, the output signals from sensors 120 are connected to pre-amplifier 130 which amplifies output signals by a predetermined amount. Output signals are then passed through to main amplifier 140 which amplifies them yet again.

In step 220 of process 280, amplified output signals are fed into a processor, such as computer 150, which digitizes the output signals.

In step 230 of process 280, computer 150 performs Fourier transformations or cross-correlations on output signals to generate a set of state variables.

The Fourier transform is a well known operation whereby the power spectral density of a signal can be obtained. The Fourier transforms of most signals have both real and imaginary components. Power spectral density is computed by taking the sum of the squares of the real and imaginary components of the Fourier transform for each frequency value of transformed output signal.

In step 240, computer 150 determines a set of state variables for each selected frequency sub-band of a selected frequency band for each of the output signals. During the training phase, in step 250, the set of state variables will be used to train neural network 280. During normal operation of neural network 280, this set of state variables will be applied to neural network 494 to determine the present will of subject 110, in step 260.

Brain waves are typically divided into several frequency bands. The alpha (α) band is a band of frequencies between about 8 Hz and about 13 Hz. The a band is an important source of information about will. In addition to the α band, there is the delta (δ) band (from about 1 to about 5 Hz), the theta (θ) band (from about 5 to about 8 Hz), the β band (from about 13 Hz to about 30 Hz) and the gamma (γ) band (above about 30 Hz). The following description employs only the α band, but the invention can be applied to any of the other bands. Characteristic values other than brain waves (for example, muscle potential, heart-rate, eye-movement and frequency of eye blinks, or any combination thereof) can also be divided into multiple frequency bands, so the following description applies.

The α band may be sub-divided into three sub-bands, $\alpha_1$, $\alpha_2$ and $\alpha_3$. Such sub-division can be accomplished by band-pass filtering. In this example the $\alpha_1$ sub-band extends from about 8 to about 9.5 Hz, the $\alpha_2$ sub-band from about 9.5 to about 11 Hz and the $\alpha_3$ sub-band from about 11 to about 13 Hz. For purposes of illustration, assume that there are six sensors 120 attached to subject 110 for each frequency band. A set of state variables can be created from cross-correlating pairs of the spectral power values of the sensor output signals. The cross-correlation operation for EEG potential $V_j$ measured at the jth electrode and the EEG potential $V_k$ measured at the kth electrode site where j=1,2, . . . , 6 and k=1,2, . . . , 6 is defined as:

$$\frac{<V_j> <V_k>}{(<V_j^2> <V_k^2>)^{0.5}}$$

where the < >operator means average over an interval, typically about 5 seconds. Similar expressions are obtained for each of the $\alpha_1$, $\alpha_2$ and $\alpha_3$ sub-bands. There are then $_6C_2=(6\times5)/2=15$ combinations of pairs of sensors 120 for each frequency band and a total of $3\times15=45$ cross-correlation coefficients which can be used as a set of state variables. Another set of 18 state variables can be generated by adding powers (mean squares) of the electric potential of each of the 6 electrodes for each of the 3 bands. In fact, a set of 63 state variables can be generated by combining the set of 45 state variables with the set of 18 state variables.

Alternatively a set of 306 state variables can be generated from the 51 values of the Fourier transformation from 5 to 15 Hz for each of the 6 sensors 120 where the Fourier transformation is performed every 5 seconds.

In step 250, computer 150 forms sets of reference weights and sets of reference biases for a neural network. Step 250 is also referred to as the neural network training phase. Each of the sets of reference weights and each of the sets of reference biases is formed from applying to the neural network a set of state reference variables corresponding to a known will.

Figure 3:
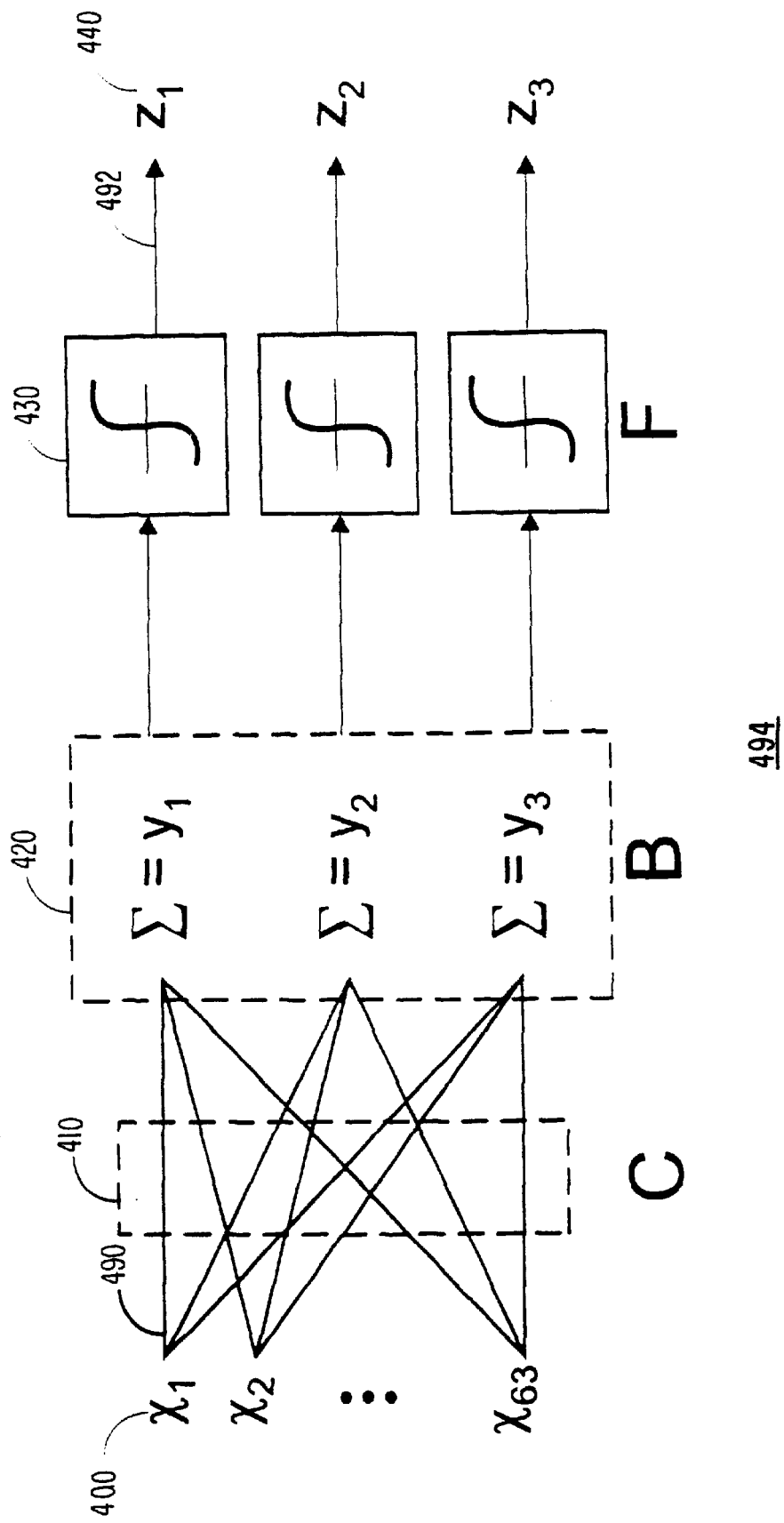
FIG. 3 shows a typical neural network.

FIG. 3 shows typical neural network 494 composed of two layers, input layer 490 and output layer 492. Neural networks with more layers and more neurons can also be used. However, output layer 492 will always comprise a neuron for each will to be determined. For example, in the case when there are two wills to be detected, output layer 492 has two neurons, rather than the three neurons shown in FIG. 3. The advantages to using neural networks are manifold. In order to build a system which can determine will information with high accuracy, the ability of a neural network to use multi-sensor inputs (scalp potential, muscle potential, heart-rate, eye-movement and frequency of eye blinks of the subject, etc) is a big advantage. Indeed, it is possible to train a neural network using incomplete, noisy, redundant or even contradictory data—a big advantage over so-called "expert-systems" which require a complex set of formal rules.

Non-linear transfer functions are sometimes used for in transfer function stage 430 to compress their inputs (which may have any value between plus and minus infinity) into the range of 0 to 1. A sigmoid transfer function can be used as the non-linear transfer function because it is differentiable. However, since the sigmoid function saturates (produces a value close to one) for most positive inputs, use of the sigmoid is function results in a loss of information about the intensity of the will. Therefore in order to preserve maximum information about the intensity of the wills, and to avoid the problems associated with a sigmoid function, the function preferably used in the transfer function stage 430 during normal operation is such that for inputs greater than or equal to zero its output is slowly saturating (for example, logarithmic or linear), while for inputs less than zero its output is zero. During the training phase, the function preferably used in transfer function stage 430 is slowly saturating (for example, logarithmic or linear) for all inputs.

Consider input layer 490 of neural network 494 composed of 63 inputs 400 $x_1, x_2, \ldots, x_3$, a weighting stage 410, a biasing and summing stage 420, a transfer function stage 430 and outputs 440 $z_1, z_2, z_3$. When there are two wills to be determined, output layer 492 comprises two outputs 440 $z_1, z_2$. In the training phase, transfer function 430 is a linear transfer function and the weights and biases are adjusted such that outputs corresponding to wills 0 and 1 approach $z=[1,0]$ and $[0,1]$, respectively. During operation of the trained neural network, function 430 is such that for inputs greater than or equal to zero its output is linear, while for inputs less than zero its output is zero.

Biases help neural network 494 to represent relationships between input 400 and output 440 more easily because a neural network layer without a bias has a net output to the following layer of zero when all of its inputs are zero.

At the start of the training phase the weights, represented by matrix C and the biases, represented by matrix B are set to random values. When the first set of state reference variables corresponding to a known will is applied to input 400 and propagated through the neural network 494, output 440 will likely not indicate the correct will. Output 440 is compared with the desired output 440 and an error is calculated. Training is completed when the difference between actual output 440 and desired output 440 is less than a selected value (calculated as the sum of the squares of the difference between desired and actual output 440). This process is repeated for the sets of state reference variables corresponding to the known wills which are to be recognized.

In step 260, computer 150 applies each of the sets of state variables to neural network 494 which is formed with the sets of reference weights and the sets of reference biases. Using neural network 494 to interpret the state variables, computer 150 is able to determine the present will of subject 110.

The operation of trained neural network 494 can be illustrated in reference to the following equations. The result of weighting stage 410 and biasing and summing stage 420 is expressed as a vector $Y=[y_1, y_2]$, whereby $$Y = \begin{bmatrix} y_1 \\ y_2 \end{bmatrix}$$
$$= CX + B$$
$$= \begin{bmatrix} c_1^1 & c_1^2 & c_1^3 & \ldots & c_1^{63} \\ c_2^1 & c_2^2 & c_2^3 & \ldots & c_2^{63} \end{bmatrix} \begin{bmatrix} x_1 \\ x_2 \\ x_3 \\ \vdots \\ x_{63+} \end{bmatrix} + \begin{bmatrix} b_1 \\ b_2 \\ b_3 \end{bmatrix}$$
$$= \begin{bmatrix} c_1^1 x_1 + c_1^2 x_2 + c_1^3 x_3 + \ldots c_1^{63} x_{63} + b_1 \\ c_2^1 x_1 + c_2^2 x_2 + c_2^3 x_3 + \ldots c_2^{63} x_{63} + b_2 \end{bmatrix}$$

Vector Y is then operated on by the linear transfer function stage 430 which creates vector Z:

$$Z = \begin{bmatrix} z_1 \\ z_2 \end{bmatrix}$$

In step 270, computer 150 displays the present will of subject 110 on display 160, as shown in FIG. 1.

Neural network 494 of FIG. 3 can recognize combinations of three different reference wills, represented by the set of output 440 vectors $Z=\{[1, 0]$ and $[0, 1]\}$. Output 440 vector, for example [0.8, 0.6], indicates that the present will of subject 110 is a weighted combination of the two reference wills. Analysis of the will can be performed in nearly real time (for example, every 5 seconds) and monitoring the time change of the will is useful for bio-feedback.

A neural network of the present invention that has been trained at a particular time to recognize certain wills of a given subject will be able to recognize any such will for that subject at any other time. Further, when the reference wills are specific enough (for example, listening to music in the right ear corresponds to "yes" and listening to music in the left ear corresponds to "no"), a neural network trained for one subject can be used for any other subject—a universal database.

Consider the application of the present invention to reading the state of mind of a subject who has lost the ability to express his/her will verbally or by bodily motion. Using the present invention, such a patient can still communicate with his/her family.

The present invention is also applicable to the problem of bio-signal control. As an example, consider a wheelchair-bound person. Using the present invention to detect the person's will, the processor can, in turn, control the direction and speed of motion of an external device (such as a wheelchair or robot) by emitting control signals which are sent to external device controller 170. Controller 170 provides the control codes necessary to operate external device actuator 180, as shown in FIG. 1.

In one embodiment, outputs corresponding to emotions such as anger, sadness, joy and disgust are allocated to the forward, backward, right and left control signals for a wheelchair or robot. The control signals can be transmitted to the controller via a wireless transceiver, which uses radio or infrared waves, for example.

It should be noted that the sensors used to detect the subject's characteristic values need not be coupled to the processor directly. Rather, the sensor signals may be transmitted by a wireless transceiver, thereby allowing the subject freedom of movement.

Thus it can be seen that a method and an apparatus for will determination and bio-signal control, and more particularly to quantifying the will of the human subject to which the apparatus is connected and allowing the subject to control elements of his environment has been described. One skilled in the art will appreciate that the present invention can be practiced by other than the described embodiments, which are presented for purposes of illustration and not of limitation, and the present invention is limited only by the claims which follow.

What is claimed is:

1. Apparatus for automatically determining a present will of a human subject, comprising:
    a plurality of sensors which detect at least one member of the group consisting of scalp potential at a plurality of points on a scalp of said subject, muscle potential at a plurality of points on a body of said subject, heart rate of said subject, eye movements of said subject, and eye blinks of said subject, and produce output signals for detecting characteristic values of said subject when affixed to a body of said subject;
    amplifiers for amplifying said output signals; and
    a processor for:
        digitizing said output signals,
        determining a set of state variables for each of a plurality of selected frequency sub-bands of a selected frequency band for each of said output signals,
        storing sets of reference weights and sets of reference biases for a neural network, wherein each of said sets of reference weights and each of said sets of reference biases is formed from a set of state reference variables corresponding to a known will, and
        applying each of said sets of state variables, said sets of reference weights and said sets of reference biases to said neural network to determine said present will of said subject.

2. The apparatus of claim 1 wherein said set of state variables comprises cross-correlating said output signals.

3. The apparatus of claim 1 wherein said set of state variables is determined by performing Fourier transformations on said output signals.

4. The apparatus of claim 1 wherein said output signals are transmitted to said processor via a wireless transceiver.

5. The apparatus of any one of claims 1 through 9 wherein said selected frequency band is a frequency band selected from the group consisting of alpha band, beta band, gamma band, delta band, theta band and mu band.

6. The apparatus of claim 1 said present wherein will of said subject is displayed.

7. The apparatus of claim 1 said present wherein will of said subject is used to control an external device.

8. A method for automatically determining a present will of a human subject, comprising the steps of:
    detecting characteristic values of said subject and producing output signals corresponding to said characteristic values, said characteristic values being at least one member of the group consisting of scalp potential at a plurality of points on a scalp of said subject, muscle potential at a plurality of points on a body of said subject, heart rate of said subject, eye movements of said subject, and eye blinks of said subject;
    amplifying said output signals;
    digitizing said output signals;
    determining a set of state variables for each of a plurality of selected frequency sub-bands of a selected frequency band for each of said output signals,
    forming sets of reference weights and sets of reference biases for a neural network from sets of state reference variables corresponding to a known will, and
    applying each of said sets of state variables, said sets of reference weights and said sets of reference biases to said neural network to determine said present will of said subject.

9. The method of claim 8 wherein said step of determining said set of state variables comprises cross-correlating said output signals.

10. The method of claim 8 wherein said step of determining said set of state variables comprises performing Fourier transformations on said output signals.

11. The method of claim 8 wherein said output signals are transmitted via a wireless transceiver for amplifying.

12. The method of claim 8 wherein said output signals are transmitted via a wireless transceiver for digitizing.

13. The method of claim 8 wherein said output signals are transmitted via a wireless transceiver for determining said set of state variables.

14. The method of any one of claims 8 through 13 wherein said selected frequency band is a frequency band selected from the group consisting of alpha band, beta band, gamma band, delta band, theta band and mu band.

15. The apparatus of claim 8 said present wherein will of said subject is displayed.

16. The apparatus of claim 8 wherein will of said subject is used to control an external device.

17. Apparatus for emitting signals based on a present will of a human subject, comprising:
    a plurality of sensors which detect at least one member of the group consisting of scalp potential at a plurality of points on a scalp of said subject, muscle potential at a plurality of points on a body of said subject, heart rate of said subject, eye movements of said subject, and eye blinks of said subject, and produce output signals for detecting characteristic values of said subject when affixed to a body of said subject;

amplifiers for amplifying said output signals;

a processor for
- digitizing said output signals,
- determining a set of state variables for each of a plurality of selected frequency sub-bands of a selected frequency band for each of said output signals,
- storing sets of reference weights and sets of reference biases for a neural network, wherein each of said sets of reference weights and each of said sets of reference biases is formed from a set of state reference variables corresponding to a known will, and
- applying each of said sets of state variables, said sets of reference weights and said sets of reference biases to said neural network to determine said present will of said subject, and a transceiver connected to said processor for emitting the control signals based on the determined will of said subject.

18. The apparatus of claim 17 wherein said set of state variables comprises cross-correlating said output signals.

19. The apparatus of claim 17 wherein said set of state variables is determined by performing Fourier transformations on said output signals.

20. The apparatus of claim 17 wherein said output signals are transmitted to said processor via a wireless transceiver.

21. The apparatus of claim 17 wherein said control signals are transmitted to a controller via a wireless transceiver.

22. The apparatus of any one of claims 17 through 21 wherein said selected frequency band is a frequency band selected from the group consisting of alpha band, beta band, gamma band, delta band, theta band and mu band.

23. The apparatus of claim 17 wherein will of said subject is displayed.

24. The apparatus of claim 17 wherein will of said subject is used to control an external device.

25. A method for emitting control signals based on a will of a human subject, comprising the steps of:

detecting characteristic values of said subject and producing output signals corresponding to said characteristic values, said characteristic values being at least one member of the group consisting of scalp potential at a plurality of points on a scalp of said subject, muscle potential at a plurality of points on a body of said subject, heart rate of said subject, eye movements of said subject, and eye blinks of said subject;

amplifying said output signals;

digitizing said output signals;

determining a set of state variables for each of a plurality of selected frequency sub-bands of a selected frequency band for each of said output signals;

forming sets of reference weights and sets of reference biases for a neural network from sets of state reference variables corresponding to known wills;

applying each of said sets of state variables, said sets of reference weights and said sets of reference biases to said neural network to determine said present will of said subject; and transmitting said control signals based on the determined will of said subject.

26. The method of claim 25 wherein said step of determining said set of state variables comprises cross-correlating said output signals.

27. The method of claim 25 wherein said step of determining said set of state variables comprises performing Fourier transformations on said output signals.

28. The method of claim 25 wherein said output signals are transmitted via a wireless transceiver for amplifying.

29. The method of claim 25 wherein said output signals are transmitted via a wireless transceiver for digitizing.

30. The method of claim 25 wherein said output signals are transmitted via a wireless transceiver for determining said set of state variables.

31. The method of any one of claims 25 through 30 wherein said selected frequency band is a frequency band selected from the group consisting of alpha band, beta band, gamma band, delta band, theta band and mu band.

32. The method of claim 25 said present wherein will of said subject is displayed.

33. The method of claim 25 the determined wherein will of said subject is used to control an external device.

* * * * *